United States Patent
Fernald et al.

(10) Patent No.: US 9,814,519 B2
(45) Date of Patent: Nov. 14, 2017

(54) ABLATION PROBE WITH RIBBED INSULATED SHEATH

(75) Inventors: Kathleen Fernald, Brookline, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2918 days.

(21) Appl. No.: 11/379,537

(22) Filed: Apr. 20, 2006

(65) Prior Publication Data

US 2007/0250053 A1    Oct. 25, 2007

(51) Int. Cl.
*A61B 18/14*    (2006.01)
*A61B 17/00*    (2006.01)
*A61B 18/00*    (2006.01)

(52) U.S. Cl.
CPC ...... *A61B 18/1482* (2013.01); *A61B 18/1477* (2013.01); *A61B 2017/00845* (2013.01); *A61B 2018/00083* (2013.01); *A61B 2018/00166* (2013.01); *A61B 2018/00577* (2013.01); *A61B 2018/1425* (2013.01)

(58) Field of Classification Search
CPC ............ A61B 18/1482; A61B 18/1477; A61B 2018/00083; A61B 2018/00166; A61B 2018/00577; A61B 2018/1425
USPC ...................................... 606/32–50
See application file for complete search history.

(56) References Cited

U.S. PATENT DOCUMENTS

| | | | | |
|---|---|---|---|---|
| 4,936,301 A | * | 6/1990 | Rexroth et al. | 606/45 |
| 5,672,173 A | * | 9/1997 | Gough et al. | 606/41 |
| 5,762,631 A | * | 6/1998 | Klein | 604/171 |
| 5,980,517 A | * | 11/1999 | Gough | 606/41 |
| 5,989,176 A | | 11/1999 | Ratzel et al. | |
| 6,066,134 A | * | 5/2000 | Eggers et al. | 606/32 |
| 6,379,353 B1 | | 4/2002 | Nichols | |

(Continued)

FOREIGN PATENT DOCUMENTS

WO    WO 2005/104973 A1    11/2005

OTHER PUBLICATIONS

PCT International Search Report for PCT/US2007/066721, Applicant: Boston Scientific Scimed, Inc., Form PCT/ISA/210 and 220, dated Nov. 15, 2007 (6 pages).

(Continued)

*Primary Examiner* — Ronald Hupczey, Jr.

(57) ABSTRACT

A tissue ablation probe comprises an electrically conductive probe shaft, at least one electrode, and an electrically insulative sheath disposed on the probe shaft. The insulative sheath has thickened regions forming alternating ribs and depressions that longitudinally extend along the probe shaft. The ribs allow the ablation probe to be delivered through a tightly toleranced delivery device. While the ribs may shear off during the delivery process, the underlying probe shaft will remain covered by the remaining portion of the insulative sheath. The tissue ablation probe may be used in a tissue ablation assembly that additionally comprises a delivery cannula having a lumen in which the tissue ablation probe may be removably disposed. In this case, the sheath has an outer periphery having a size substantially the same as the diameter of the lumen, so that the inner surface of the delivery cannula cooperates with the depressions to create lumens that longitudinally extend within the cannula.

13 Claims, 9 Drawing Sheets

(56) References Cited

U.S. PATENT DOCUMENTS

| | | | |
|---|---|---|---|
| 6,398,759 B1 | 6/2002 | Sussman et al. | |
| 6,743,206 B1* | 6/2004 | Smith et al. | 604/164.01 |
| 7,282,051 B2 | 10/2007 | Rioux et al. | |
| 7,425,212 B1* | 9/2008 | Danek et al. | 606/47 |
| 2002/0072737 A1* | 6/2002 | Belden et al. | 606/34 |
| 2005/0171526 A1 | 8/2005 | Rioux et al. | |
| 2005/0234298 A1* | 10/2005 | Kucklick et al. | 600/156 |
| 2005/0234443 A1 | 10/2005 | Rioux et al. | |
| 2006/0149226 A1 | 7/2006 | McCullagh et al. | |
| 2007/0093802 A1* | 4/2007 | Danek et al. | 606/41 |

OTHER PUBLICATIONS

PCT Written Opinion of the International Search Authority for PCT/US2007/066721, Applicant: Boston Scientific Scimed, Inc., Form PCT/ISA/237, dated Nov. 15, 2007 (8 pages).

PCT International Preliminary Report on Patentability (Chapter I of the Patent Cooperation Treaty) for PCT/US2007/066721, Applicant: Boston Scientific Scimed, Inc., Form PCT/IB/326, dated Oct. 30, 2008 (6 pages).

\* cited by examiner

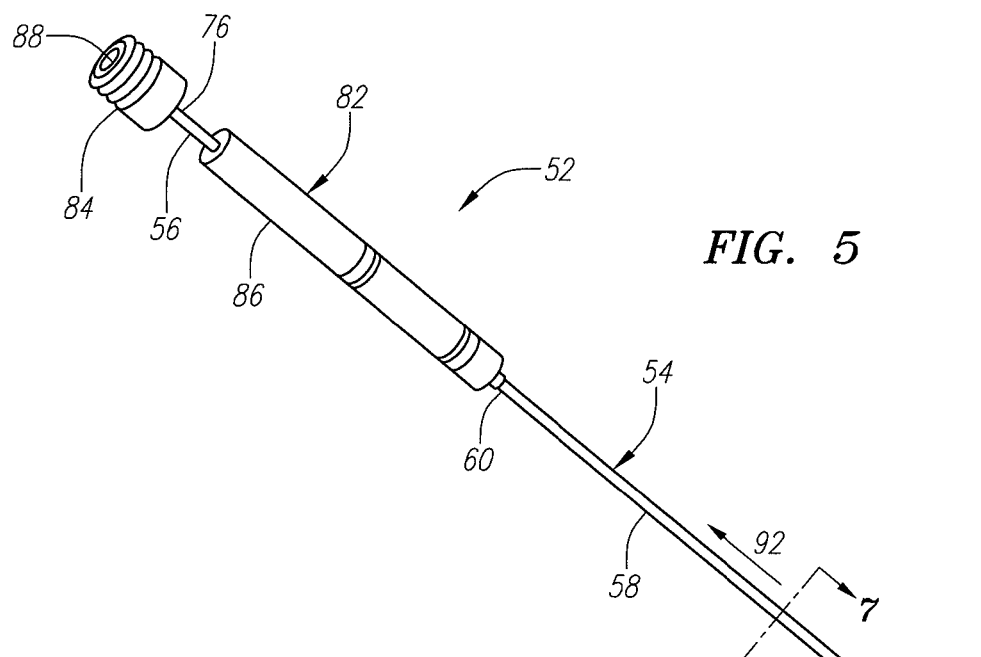
FIG. 5
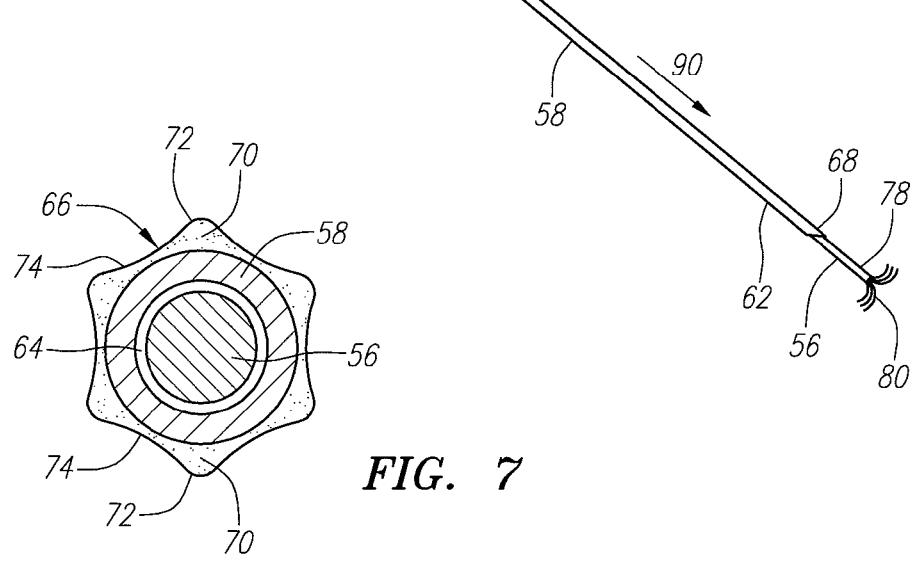
FIG. 6
FIG. 7

ABLATION PROBE WITH RIBBED INSULATED SHEATH

FIELD OF THE INVENTION

The field of the invention relates generally to the structure and use of radio frequency (RF) ablation probes for the treatment of tissue.

BACKGROUND OF THE INVENTION

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from an exposed, uninsulated portion of the electrode. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a cannula and an electrode deployment member reciprocatably mounted within the delivery cannula to alternately deploy an electrode array from the cannula and retract the electrode array within the cannula. Using either of the two technologies, the energy that is conveyed from the electrode(s) translates into ion agitation, which is converted into heat and induces cellular death via coagulation necrosis. The ablation probes of both technologies are typically designed to be percutaneously introduced into a patient in order to ablate the target tissue.

Because the size of tissue coagulation created from a single electrode, and to a lesser extent a multiple electrode array, has been limited by heat dispersion, it is known to introduce an electrically conductive fluid, such as saline, into targeted tissue to increase the tissue conductivity, thereby creating a larger lesion size. It has been shown that the introduction of saline into targeted tissue during an ablation procedure increases the tissue conductivity, thereby creating a larger lesion size. Saline can be introduced into the tissue using a separate device, such as a syringe, or can be perfused from the ablation probe itself.

When designing RF ablation probes using either of the two technologies, RF energy is often delivered to the distal electrode(s) via the shaft itself, thereby requiring the probe to be electrically insulated to prevent undesirable ablation of healthy tissue. In the case of a single needle electrode, all by the distal tip of the electrode is coated with an electrically insulative material in order to focus the RF energy at the target tissue located adjacent the distal tip. In the case of a LeVeen Needle Electrode™, RF energy is conveyed to the needle electrodes through the inner electrode deployment member, and the outer cannula is coated with the electrically insulative material to prevent RF energy from being transversely conveyed from the inner electrode deployment member along the length of the probe. When designing RF ablation probes, it is also desirable to make the profile of the probe shaft as small as possible in order to minimize any pain and tissue trauma resulting from the percutaneous insertion of the probe into the patient to be treated. Thus, it is advantageous that the electrically insulative material applied to the probes be as thin as possible. However, RF ablation probes are often introduced through other tightly toleranced devices that may compromise the integrity of the thinly layered insulation, thereby inadvertently exposing healthy tissue to RF energy.

For example, probe guides are often used to point ablation probes towards the target tissue within a patient. A typical probe guide takes the form of a rigid cylindrical shaft (about 1-2 inches in length) that is affixed relative to and outside of a patient, and includes a lumen through which the ablation probe is delivered to the target tissue. To maximize the accuracy of the probe alignment, it is desirable that the guide lumen through which the probe is introduced be about the same size as the outer diameter of the probe, thereby creating a tight tolerance between the probe and the probe guide. As another example, ablation probes are also often used with co-access assemblies that allow several different devices, such as ablation probes, biopsy stylets, and drug delivery devices, to be serially exchanged through a single delivery cannula. To minimize pain and tissue trauma, it is desirable that the profile of the delivery cannula be as small as possible. As a result, the lumen of the delivery cannula will typically be the same size as the outer diameter of the ablation probe, thereby creating a tight tolerance between the probe and the delivery cannula.

Thus, during the initial introduction of the probe through a delivery device, such as a probe guide or cannula of a co-access system, it is possible for the proximal edge of the probe guide to catch the distal edge of the insulation that coats the probe. If this occurs, a portion of the insulation may shear off as the probe is introduced through the delivery device. As a result, the attending physician will either have to replace the probe with a new one or risk ablating healthy tissue.

In addition, as discussed above, it is often desirable to deliver an electrically conductive fluid to the target tissue to facilitate the tissue ablation process. In the case where a co-access assembly is used, it has been proposed that the electrically conductive fluid could be introduced through either the co-access cannula or the ablation probe. However, equipping the cannula with lumens will ultimately increase its profile, thereby increasing the pain and tissue trauma associated with the percutaneous introduction of the cannula into the patient. It may be possible to equip the ablation probe with lumens. However, in the case of LeVeen Needle Electrodes™, every diminutive amount of space inside the cannula of the RF probe must be utilized by the needle electrodes, and therefore, it is difficult to design lumens within such probes.

There, thus, is a need for an improved ablation probe that minimizes the chance of inadvertent ablation of healthy tissue caused by the shearing of electrical insulation and/or an ablation probe that facilitates the delivery of an electrically conductive fluid when combined in a co-access ablation assembly.

SUMMARY OF THE INVENTION

In accordance with a first aspect of the present inventions, a tissue ablation probe comprises an electrically conductive probe shaft, at least one electrode, and an electrically insulative sheath disposed on the probe shaft. The electrode(s) may, e.g., be a single needle electrode disposed at an uninsulated distal end of the probe shaft. The ablation probe may further comprise an electrical connector carried by a proximal end of the probe shaft, wherein the electrical connector is electrically coupled to the electrode(s) through the probe shaft.

In one embodiment, the electrically insulative sheath is fixably disposed on the probe shaft. Preferably, the probe shaft is rigid and cylindrical, although the probe shaft may alternatively have other cross-sectional shapes and may be semi-rigid or flexible. The ablation probe may, e.g., comprise a single probe shaft, or the probe shaft may take the form of a cannula, in which case, the ablation probe may further comprise an inner probe shaft slidably disposed within the cannula. In the latter case, the electrode(s) may be disposed on the inner probe shaft and may be deployable from the cannula.

The insulative sheath has thickened regions forming alternating ribs and depressions that longitudinally extend along the probe shaft. The ribs and depressions may extend substantially the entire length of the probe shaft. While the present inventions should not be so limited in their broadest aspects, the ribs allow the ablation probe to be delivered through a tightly toleranced delivery device. While the ribs may shear off during the delivery process, the underlying probe shaft will remain covered by the remaining portion of the insulative sheath, thereby minimizing the chance that healthy tissue may be inadvertently ablated.

The tissue ablation probe may be used in a tissue ablation assembly that additionally comprises a delivery cannula having a lumen in which the tissue ablation probe may be removably disposed. In this case, the sheath has an outer periphery having a size substantially the same as the diameter of the lumen, so that the inner surface of the delivery cannula cooperates with the depressions to create lumens that longitudinally extend within the cannula.

The tissue ablation probe may also be used in a method to ablate tissue. The method may comprise introducing the tissue ablation probe through a delivery device into a tissue region, e.g., percutaneously, and ablating the tissue region with the electrode(s). During delivery of the tissue ablation probe, at least a portion of one of the ribs is sheared off by movement of the tissue ablation probe through the delivery device without exposing an underlying region of the probe shaft.

In accordance with a second aspect of the present inventions, a tissue ablation probe assembly comprises a cannula having a delivery lumen extending therethrough, and a tissue ablation probe configured to be removably received within the cannula. The tissue ablation probe has an outer electrically insulative surface having a plurality of longitudinally extending depressions that cooperate with an inner surface of the cannula to form a plurality of lumens. The tissue ablation probe assembly further comprises at least one fluid infusion port coupled to the plurality of lumens. The construction of the tissue ablation probe may be similar to the tissue ablation probe described above. Although the present inventions should not be so limited in their broadest aspects, the depressions provide a convenient and efficient means of incorporating fluid lumens within the probe assembly.

The tissue ablation probe assembly may be used in a method of ablating tissue. Such method comprises introducing the cannula into a patient adjacent a tissue region, introducing the tissue ablation probe through the cannula into contact with the tissue region, introducing fluid into the infusion port(s), whereby the fluid flows through the lumens into contact with the tissue region, and ablating the tissue region with the tissue ablation probe. The fluid may be electrically conductive to facilitate the ablation process and/or may contain one or more chemotherapeutic agents to further treat the tissue.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 5 is a perspective view of another tissue ablation probe that can be used within the tissue ablation system of FIG. 1, wherein an electrode array is particularly shown retracted;

FIG. 6 is a perspective view of the tissue ablation probe of FIG. 5, wherein the electrode array is particularly shown deployed;

FIG. 7 is a cross-sectional view of the tissue ablation probe of FIG. 5, taken along the line 7-7;

DETAILED DESCRIPTION OF THE EMBODIMENTS

Figure 1:
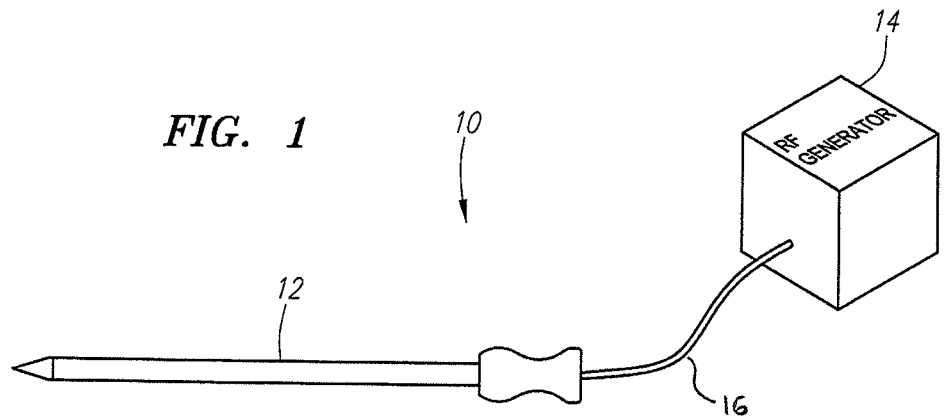
FIG. 1 is a plan view of a tissue ablation system arranged in accordance with one embodiment of the present inventions.

Referring to FIG. 1, a tissue ablation system 10 constructed in accordance with one embodiment of the present inventions, will now be described. The tissue ablation system 10 generally comprises an ablation probe 12 configured for introduction into the body of a patient for ablative treatment of target tissue, a source of ablation energy, and in particular a radio frequency (RF) generator 14, and a cable 16 electrically connecting the ablation probe 12 to the RF generator 14.

Figure 2:
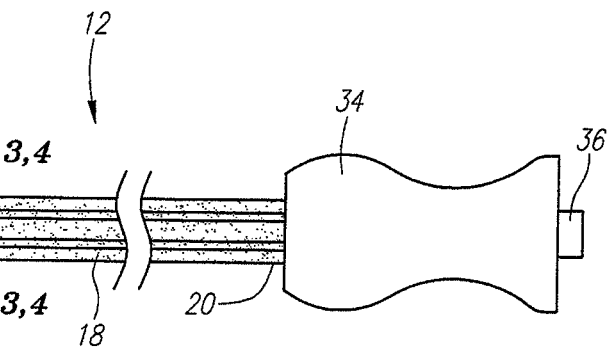
FIG. 2 is a side view of a tissue ablation probe used in the tissue ablation system of FIG. 1.

Referring now to FIG. 2, the ablation probe 12 will be described in further detail. The ablation probe 12 comprises an elongated, probe shaft 18 having a proximal end 20 and a distal end 22. The probe shaft 18 is composed of an electrically conductive material, such as stainless steel. The probe shaft 18 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

The ablation probe 12 further comprises a sheath 24 disposed on the probe shaft 18. In the illustrated embodiment, the sheath 24 is affixed to the probe shaft 18, and may be applied to the probe shaft 18 using any suitable means. For example, the insulative sheath 24 can be applied to the probe shaft 18 as a heat shrink or can be extruded onto the probe shaft 18. The sheath 24 is composed of an electrically insulative material, such as Fluorinated Ethylene Propylene (FEP), and extends the entire length of the probe shaft, with the exception of a distal tip of the probe shaft 18. In this manner, an RF ablation electrode 26 is formed by the exposed portion of the distal tip.

Figure 3:
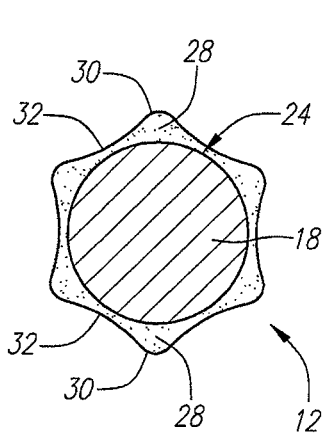
FIG. 3 is a cross-sectional view of the tissue ablation probe of FIG. 2, taken along the line 3-3, particularly showing all of the ribs fully intact.

As best shown in FIG. 3, the insulative sheath 24 has a plurality of thickened regions 28 that form a plurality of alternating ribs 30 and depressions 32 longitudinally extending along the probe shaft 18. In the illustrated embodiment, the ribs 30 and depressions 32 extend substantially the entire length of the probe shaft 18. In the illustrated embodiment, the depressions 32 are concave, although other shapes are contemplated.

Figure 4:
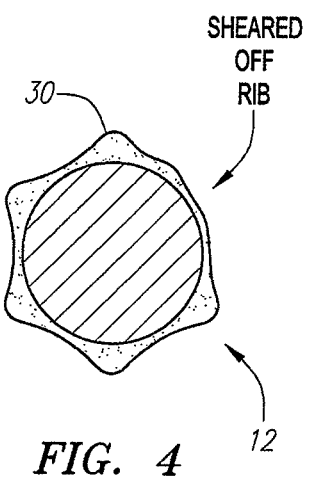
FIG. 4 is a cross-sectional view of the tissue ablation probe of FIG. 2, taken along the line 4-4, particularly showing one of the ribs sheared off.

Significantly, the ribs 30 allow the ablation probe 12 to be introduced through a delivery device, such as a probe guide or a delivery cannula under tight tolerances, while allowing portions of the insulative sheath 24 adjacent the ribs 30 to shear off as the ablation probe 12 is introduced through the delivery device without exposing the underlying probe shaft 18. For example, as illustrated in FIG. 4, no portion of the probe shaft 18 is exposed even though one of the ribs 30 has been sheared off.

The distal tip of the probe shaft 18 is a tissue-penetrating tip, which allows the ablation probe 12 to be more easily introduced through tissue, while minimizing tissue trauma. The probe shaft 18 is preferably composed of a rigid or semi-rigid material, such that the ablation probe 12 can be introduced through solid tissue to a target tissue site. Alternatively, the ablation probe 12 may be introduced through the tissue with the aid of a cannula and trocar assembly, in which case, the probe shaft 18 may be composed of a flexible material, and the distal end 22 may be blunted.

The ablation probe 12 further comprises a handle 34 mounted to the proximal end 20 of the probe shaft 18. The handle 34 is preferably composed of a durable and rigid material, such as medical grade plastic, and is ergonomically molded to allow a physician to more easily manipulate the ablation probe 12. The handle 34 comprises an electrical connector 36 with which the cable 16 (shown in FIG. 1) mates. Alternatively, the RF cable 16 may be hardwired within the handle 34. The electrical connector 36 is electrically coupled to the ablation electrode 26 via the probe shaft 18, with the insulative sheath 24 operating to focus RF energy at the electrode 26 where the targeted tissue presumably lies.

In the illustrated embodiment, the RF current is delivered to the electrode 26 in a monopolar fashion, which means that current will pass from the electrode 26, which is configured to concentrate the energy flux in order to have an injurious effect on the surrounding tissue, and a dispersive electrode (not shown), which is located remotely from the electrode 26 and has a sufficiently large area (typically 130 cm$^2$ for an adult), so that the current density is low and non-injurious to surrounding tissue. The dispersive electrode may be attached externally to the patient, e.g., using a contact pad placed on the patient's flank.

Referring back to FIG. 1, the RF generator 14 may be a conventional general purpose electrosurgical power supply operating at a frequency in the range from 300 kHz to 9.5 MHz, with a conventional sinusoidal or non-sinusoidal wave form. Such power supplies are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying an ablation current at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Therapeutics Corporation. Preferred power supplies are models RF-2000 and RF-3000, available from Boston Scientific Corporation.

Referring now to FIGS. 5 and 6, another tissue ablation probe 52 that can be used in conjunction with the RF generator 14 to create an alternative tissue ablation system will be described. The tissue ablation probe 52 includes an elongated cannula 54 and an inner probe shaft 56 slidably disposed within the cannula 54. The cannula 54 includes an elongate shaft 58 having a proximal end 60, a distal end 62, and a central lumen 64 (shown in FIG. 7), and an electrically insulative sheath 66 (shown in FIG. 7) disposed on the cannula shaft 58.

The cannula shaft 58, itself, is composed of an electrically conductive material, such as stainless steel. The material from which the cannula shaft 58 is composed is preferably a rigid or semi-rigid material, such that the ablation probe 52 can be introduced through solid tissue to a target tissue site. The distal end 62 of the cannula shaft 58 comprises a tissue-penetrating tip 68, which allows the ablation probe 52 to be more easily introduced through tissue, while minimizing tissue trauma. Alternatively, the ablation probe 52 may be introduced through the tissue with the aid of another cannula and trocar assembly, in which case, the cannula shaft 58 may be composed of a flexible material, and the distal end 62 may be blunted. The cannula shaft 58 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm.

In the illustrated embodiment, the insulative sheath 66 is affixed to the cannula shaft 58, and may be applied to the cannula shaft 58 using any suitable means, e.g., as a heat shrink or extrusion. The insulative sheath 66 has a geometry similar to that of the insulative sheath 66 described above. In particular, as best shown in FIG. 7, the insulative sheath 66 has a plurality of thickened regions 70 that form alternating ribs 72 and depressions 74 longitudinally extending along the cannula shaft 58. In the illustrated embodiment, the ribs 72 and depressions 74 extend substantially the entire length of the cannula shaft 58. In the illustrated embodiment, the depressions 74 are concave, although other shapes are contemplated. The ribs 72 provide similar advantages as those discussed above with respect to the ribs 30 of the ablation probe 12. That is, the ribs 72 allow the ablation probe 52 to be introduced through a delivery device, such as a probe guide or a delivery cannula under tight tolerances, while allowing portions of the insulative sheath 66 adjacent the ribs 72 to shear off as the ablation probe 52 is introduced through the delivery device without exposing the underlying cannula shaft 58.

The inner probe shaft 56 is slidably disposed within the cannula lumen 64 and has a proximal end 76 and a distal end 78, and an array of electrode tines 80 carried by the distal end 78 of the probe shaft 56. Like the cannula shaft 58, the inner probe shaft 56 is composed of an electrically conductive material, such as stainless steel. The inner probe shaft 56 is composed of a suitably rigid material, so that it has the required axial strength to be slide within the cannula lumen 64.

The ablation probe 52 further includes a handle assembly 82, which includes a handle member 84 mounted to the proximal end 76 of the inner probe shaft 56, and a handle sleeve 86 mounted to the proximal end 60 of the cannula 54. The handle member 84 is slidably engaged with the handle sleeve 86 (and the cannula 54). The handle member 84 and handle sleeve 86 can be composed of any suitable rigid material, such as, e.g., metal, plastic, or the like. The handle assembly 82 also includes an electrical connector 88 mounted within the handle member 84. The electrical connector 88 is electrically coupled to the electrode array 80 via the inner probe shaft 56, with the insulative sheath 66 operating to focus RF energy at the electrode array 80 where the targeted tissue presumably lies. The electrical connector 88 is configured for mating with the proximal end of the RF cable 16 (shown in FIG. 1). Alternatively, the RF cable 16 may be hardwired within the handle member 84. Like the previous described ablation probe 52, RF current may be delivered to the electrode array 80 in a monopolar fashion, It can be appreciated that longitudinal translation of the probe shaft 56 relative to the cannula 54 in a distal direction 90 can be achieved by holding the handle sleeve 86 and displacing the handle member 84 in the distal direction 90, thereby deploying the electrode array 80 from the distal end 62 of the cannula shaft 58 (FIG. 6), and longitudinal translation of the probe shaft 56 relative to the cannula 54 in a proximal direction 92 can be achieved by holding the handle sleeve 86 and displacing the handle member 84 in the proximal direction 92, thereby retracting the probe shaft 56 and the electrode array 80 into the distal end 62 of the cannula shaft 58 (FIG. 5).

Further details regarding electrode array-type probe arrangements are disclosed in U.S. Pat. No. 6,379,353, which is hereby expressly incorporated by reference.

Having described the structure of the tissue ablation system 10, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$ The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 8A:
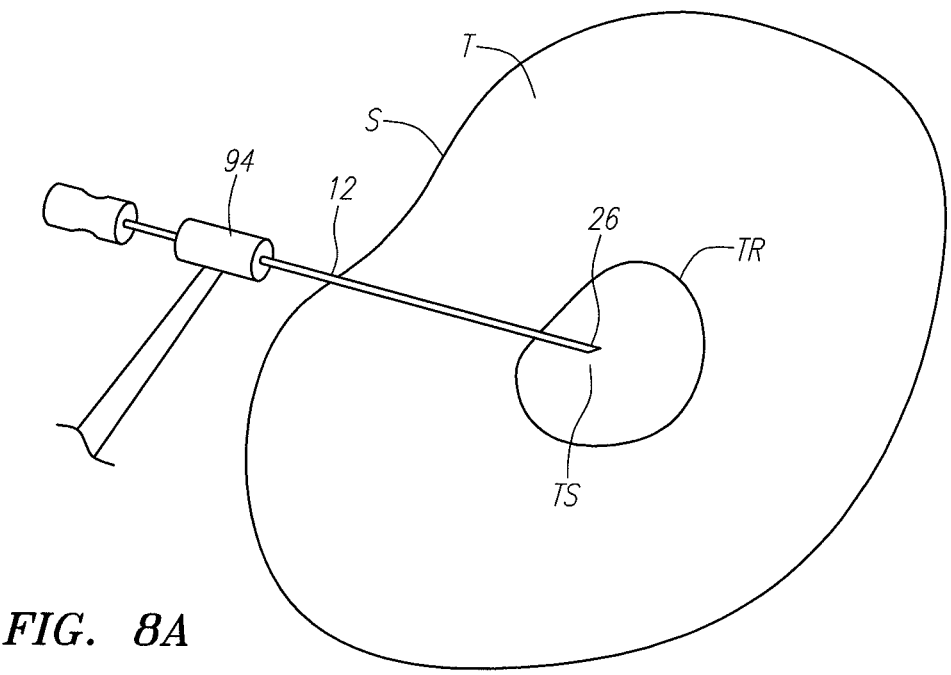
FIGS. 8A-8C illustrate cross-sectional views of one method of using the tissue ablation system of FIG. 1 to treat tissue.
Figure 8B:
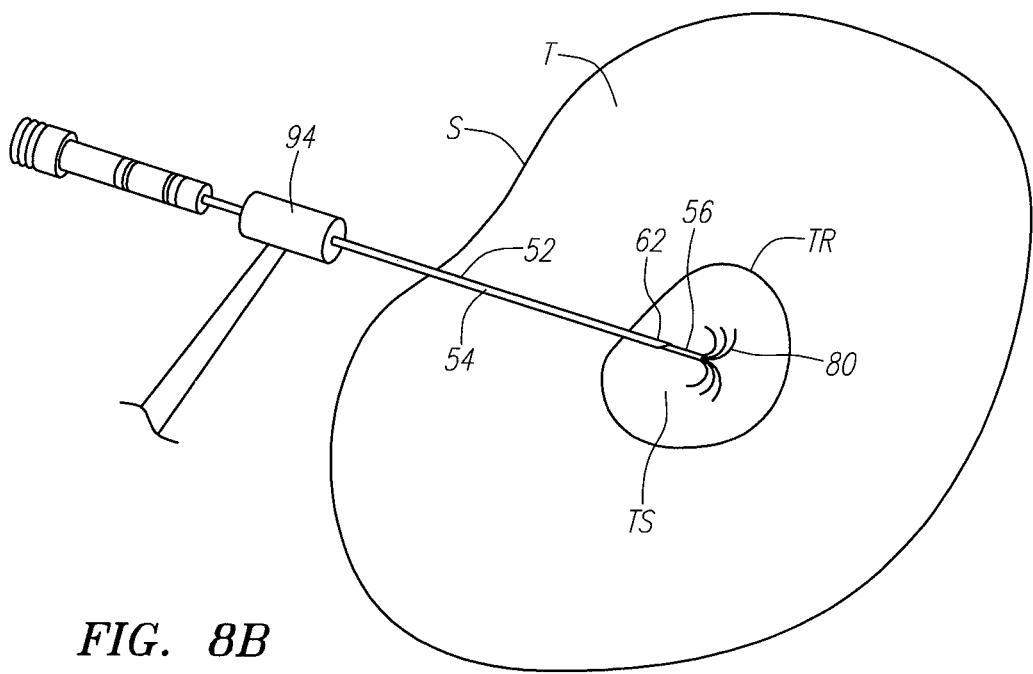
Figure 8C:
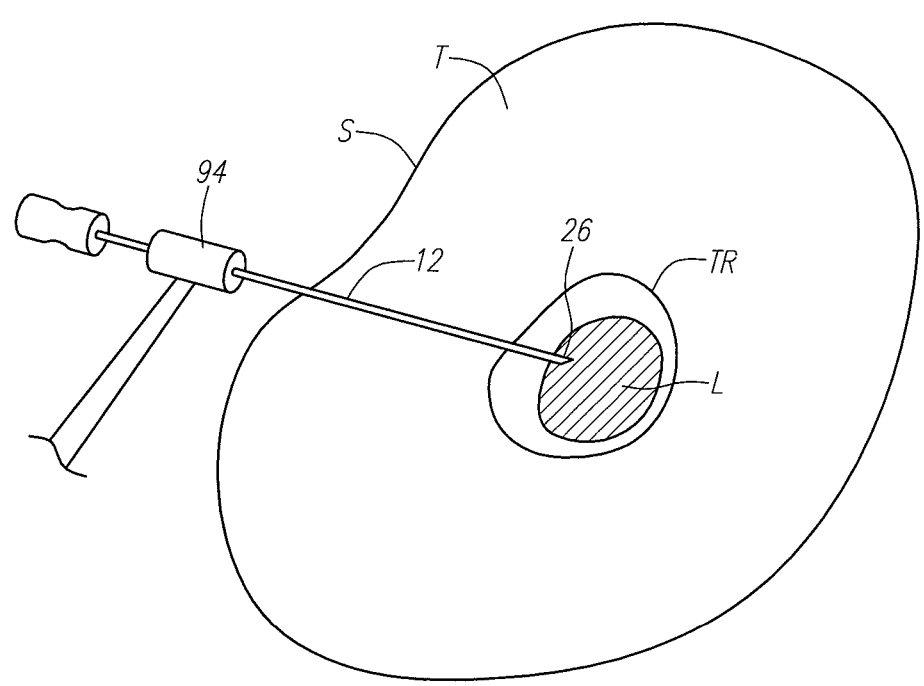

Referring now to FIGS. 8A-8C, the operation of the tissue ablation system 10 is described in treating a treatment region TR with tissue T located beneath the skin or an organ surface S of a patient. The ablation probe 12 is first introduced through the tissue T, so that the electrode 26 is located at a target site TS within the treatment region TR, as shown in FIG. 8A. This can be accomplished using any one of a variety of techniques. In the preferred method, a probe guide 94 is used to guide the ablation probe 12 towards the target site TS. In particular, the probe guide 94 is affixed and aligned relative to the target site TS, and the ablation probe 12 is introduced through the probe guide 94. Facilitated by the sharpened distal tip, the ablation probe 12 is percutaneously introduced through the patient's skin until the electrode 26 is located in the treatment region TR. Alternatively, if the ablation probe 52 illustrated in FIGS. 5 and 6 is used, the cannula 54 can be introduced through the probe guide 94 until the distal end 62 of the cannula 54 is located at the target site TS, after which the inner probe shaft 56 can be distally advanced through the cannula 54 to deploy the electrode array 80 out from the distal end 62 of the cannula 54, as shown in FIG. 8C.

As previously discussed above, any shearing of the insulative sheath 66 caused by introduction of the ablation probe 52 (or alternatively the ablation probe 52) through the probe guide 94 will occur at one of the ribs 30, thereby preventing the underlying probe shaft 56 from becoming exposed. Once the ablation probe 52 is properly positioned, the cable 16 of the RF generator 14 (shown in FIG. 1) is then connected to the electrical connector 88 of the ablation probe 12, and then operated to transmit RF energy to the electrode 26, thereby ablating the treatment region TR, as illustrated in FIG. 8C. As a result, a lesion L will be created, which will eventually expand to include the entire treatment region TR.

Figure 9:
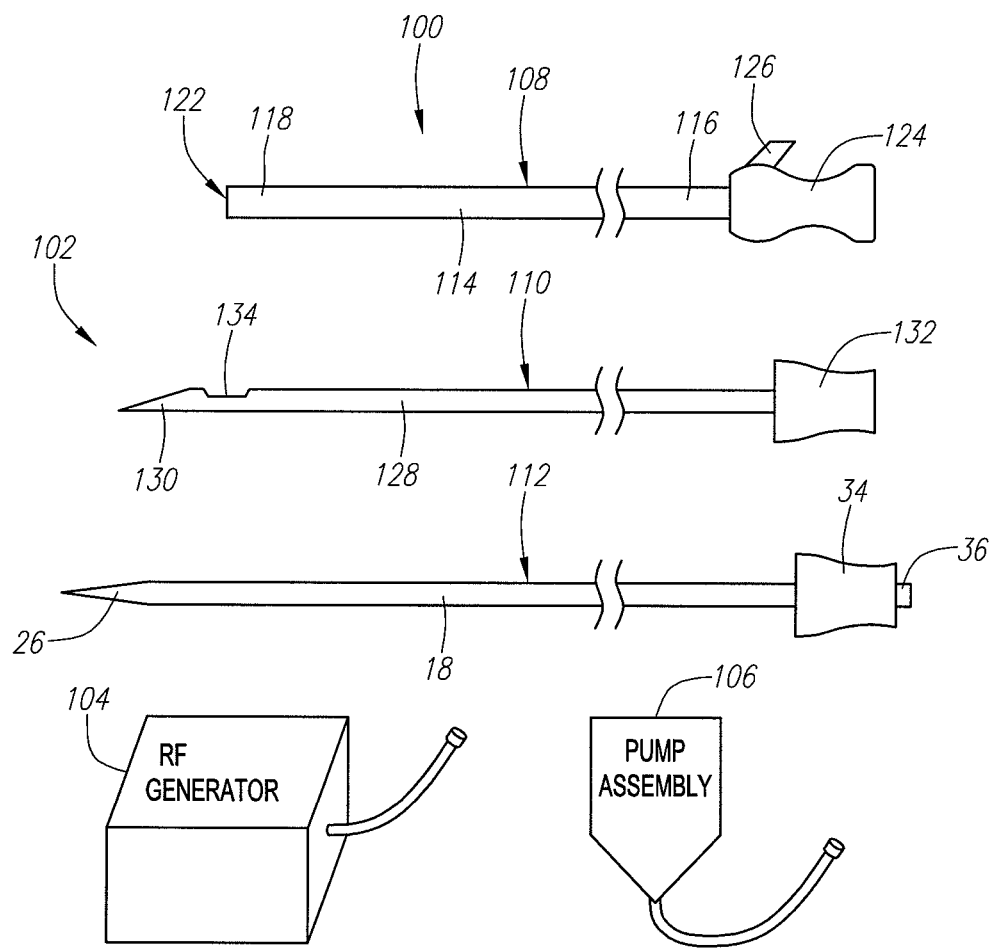
FIG. 9 is a plan view of a tissue ablation system arranged in accordance with another embodiment of the present inventions.

Referring to FIG. 9, a tissue ablation system 100 constructed in accordance with another embodiment of the present invention will now be described. The tissue ablation system 100 generally comprises a co-access probe assembly 102 configured for introduction into the body of a patient for ablative treatment of target tissue, a radio frequency (RF) generator 104 configured for supplying RF energy to the tissue ablative component of the probe assembly 102 in a controlled manner; and a pump assembly 106 configured for perfusing fluid, such as saline, out through the probe assembly 102, so that a more efficient and effective ablation treatment is effected.

The RF generator 104 is similar to the previously described RF generator 14, and will thus, not be described in further detail. The pump assembly 106 may be any type that can convey a fluid under pressure. Details regarding pump assemblies are disclosed in U.S. patent application Ser. No. 10/772,040, which is expressly incorporated herein by reference. Alternatively, rather than a pump assembly, a saline bag can simply be raised above the patient a sufficient height to provide the head pressure necessary to convey the fluid under pressure. The pump assembly 106, along with the RF generator 104, can include control circuitry to automate or semi-automate the perfused ablation process.

The co-access probe assembly 102 generally comprises a delivery cannula 108 that can be percutaneously introduced within a patient, a biopsy stylet 110 configured for removing a tissue sample from the patient, and an ablation probe 112 configured for therapeutically ablating tissue. The biopsy stylet 110 and ablation probe 112 are configured to be alternately introduced through the delivery cannula 108 in contact with the tissue to be treated.

The delivery cannula 108 comprises a cannula shaft 114 having a proximal end 116 and a distal end 118, and a delivery lumen 120 (shown in FIG. 10) extending through the cannula shaft 114. As will be described in further detail below, the cannula shaft 114 may be rigid, semi-rigid, or flexible, depending upon the designed means for introducing the delivery cannula 108 to the target tissue. The cannula lumen 120 terminates at an axial opening 122 located at the distal tip of the cannula shaft 114. As will be described in further detail below, the axial opening 122 serves as a port out which respective operative elements of the biopsy stylet 110 and ablation probe 112, as well as any fluids and/or chemotherapeutic agents, are delivered to a targeted tissue region. As will be described in further detail below, either the biopsy stylet 110 or the ablation probe 152 can be used to facilitate the percutaneous introduction of the delivery cannula 108, which has a blunt end.

In the preferred embodiment, the cannula shaft 114 is composed of an electrically conductive material, such as stainless steel. In this case, the exterior surface of the cannula shaft 114 is preferably composed of an electrically insulative material. Alternatively, the cannula shaft 114 may be composed of an electrically insulative material, such as a medical grade plastic, in which case, a separate insulative coating is not needed. The cannula shaft 114 has a suitable length, typically in the range from 5 cm to 30 cm, preferably from 10 cm to 20 cm, an outside diameter consistent with its intended use, typically being from 1 mm to 5 mm, usually from 1.3 mm to 4 mm, and an inner diameter typically being from 0.7 mm to 4 mm, preferably from 1 mm to 3.5 mm.

The delivery cannula 108 further comprises a handle 124 mounted to the proximal end 116 of the cannula shaft 114. The handle 124 is preferably composed of a durable and rigid material, such as medical grade plastic, and is ergonomically molded to allow a physician to more easily manipulate the cannula 108. The handle 124 comprises a fluid inlet port 126, so that the delivery cannula 108 can be used to deliver fluids, such as an electrically conductive fluid or chemotherapeutic agents to tissue. As will be described in further detail below, the biopsy stylet 110 and ablation probe 112 can be interchangeably introduced into the cannula lumen 120.

Referring still to FIG. 9, the biopsy stylet 110 comprises a solid elongated shaft 128 with a tissue-penetrating distal tip 130 and a proximal handle piece 132. The biopsy stylet 110 may operated in a standard manner to obtain a tissue sample. For example, in the illustrated embodiment, the biopsy stylet 110 comprises a grooved notch 134 just proximal to the distal tip 130. When the stylet 110 is advanced from the delivery cannula 108 to expose the notch 134, the tissue prolapses into the notch 134, and then the delivery cannula 108 can be advanced, thereby shearing the tissue to sever the sample. The sample is held protected inside the notch 134. The stylet 110 can then be removed from the cannula lumen 120 in order to retrieve the tissue sample. Further details regarding the structure and use of biopsy stylets in association with cannulae are disclosed in U.S. Pat. No. 5,989,196, which is expressly incorporated herein by reference.

Figure 10:
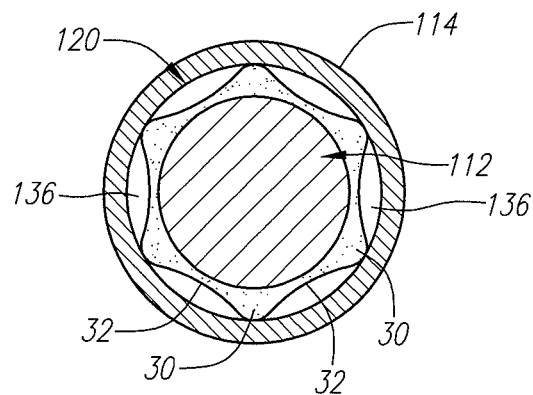
FIG. 10 is a cross-sectional view of the combination of the delivery cannula and tissue ablation probe used in the tissue ablation system of FIG. 9.

The ablation probe 112 is similar to the ablation probe 12 illustrated in FIG. 1, with the exception that the outer periphery of the ablation probe 12 is sized to snugly fit within the cannula lumen 120, as illustrated in FIG. 10. In this manner, the depressions 32 formed between the ribs 30 of the insulative sheath 24 cooperate with the inner surface of the cannula 108 to form a plurality of longitudinally extending perfusion lumens 136 that terminate at distally disposed fluid exit ports (not shown). Significantly, because the fluid inlet port 126 located on the handle 124 of the cannula 108 is in fluid communication with the cannula lumen 120, it is conveniently in fluid communication with the perfusion lumens 136 when the ablation probe 12 is mated with the cannula 108. Notably, the closed tissue-penetrating tip of the probe shaft 18 allows the cannula 108, in combination with the ablation probe 12 to be more easily introduced through tissue, while preventing tissue coring and minimizing tissue trauma.

Figure 11:
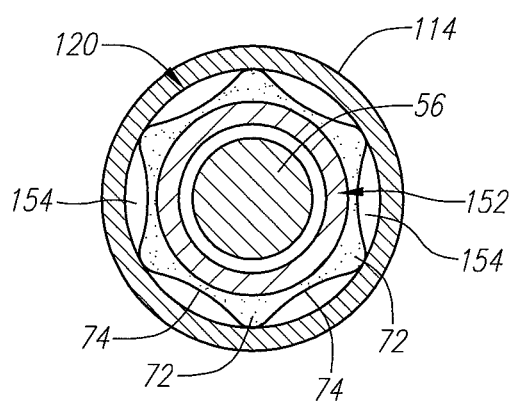
FIG. 11 is a cross-sectional view of the combination of the delivery cannula and another tissue ablation probe that could be used in the tissue ablation system of FIG. 9.

Alternatively, as illustrated in FIG. 11, a tissue ablation probe 152 similar to the probe 52 illustrated in FIGS. 5 and 6 can be utilized in the co-access probe assembly 102. In a manner similar to that described above with respect to the ablation probe 52, the recesses 74 formed between the ribs 72 of the insulative sheath 66 cooperate with the inner surface of the cannula 108 to form a plurality of longitudinally extending lumens 154 in fluid communication between the fluid inlet port 126 of the cannula 108 and distally disposed fluid exit ports. Because the ablation probe 152 has an open-ended distal tip, an obturator, e.g., a conventional trocar (not shown), can be used to facilitate the percutaneous introduction of the delivery cannula 108 into the patient's body. The use of a separate trocar may also allow the probe shaft to be composed of a flexible material and/or the distal end of the probe shaft to be blunted.

In the embodiment illustrated in FIG. 9, electrical current is delivered to the electrode 26 of the tissue ablation probe 112 in a monopolar fashion. Alternatively, a separate electrode may be formed at the distal end of the delivery cannula 108, in which case, electrical energy can be delivered between the electrode 26 of the ablation probe 112 and the electrode of the delivery cannula 108 in a bipolar fashion. Further details regarding the use of co-access cannulae to provide bipolar capability to ablation probes is described in U.S. patent application Ser. Nos. 10/828,032 and 11/030,229, which are expressly incorporated herein by reference.

Figure 12A:
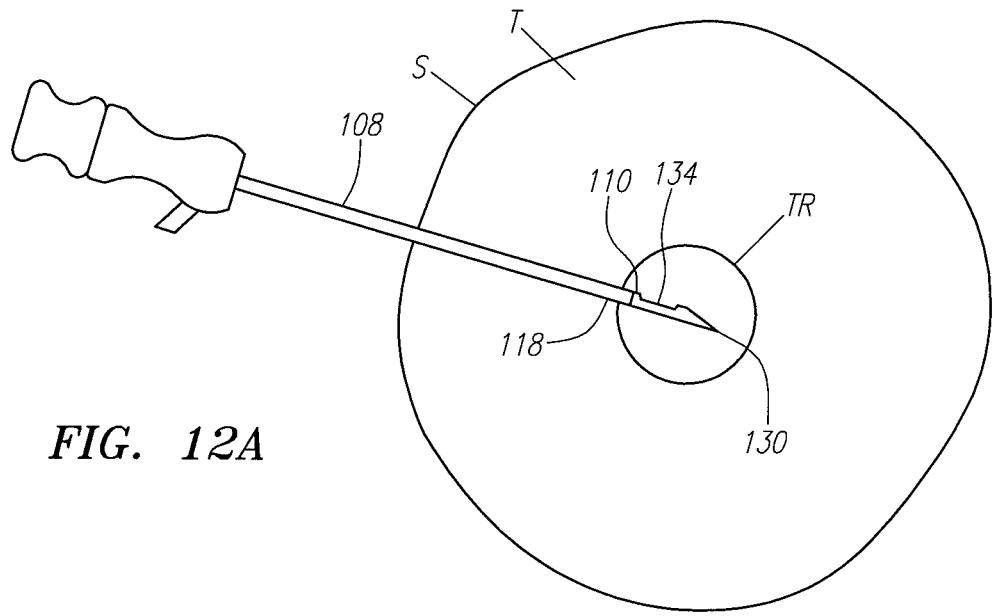
FIGS. 12A-12E illustrate cross-sectional views of one method of using the tissue ablation system of FIG. 9 to treat tissue.

Having described the structure of the tissue ablation system 100, its operation in treating targeted tissue will now be described with reference to FIGS. 12A-12E. As before stated, the treatment region may be located anywhere in the body where hyperthermic exposure may be beneficial, and can be identified using conventional imaging techniques. The delivery cannula 108 is first percutaneously introduced through the tissue T directly through the patient's skin, so that the distal end 118 of the delivery cannula 108 is located at the tissue region TR, and preferably in the center of the tissue region TR, as illustrated in FIG. 12A. This can be accomplished using any one of a variety of techniques. In the preferred method, the biopsy stylet 110 is introduced into the delivery lumen 120 of the cannula 108, and then the cannula 108 with the stylet 110, is introduced to the treatment region TR percutaneously directly through the patient's skin or through an open surgical incision. In this case, the sharpened tip 130 of the stylet 110 facilitates introduction to the treatment region TR. Alternatively, the ablation probe 112 or a trocar (not shown) can be introduced into the delivery lumen 120 of the cannula 108, in which case, the cannula 108 with the ablation probe 112 or trocar, can be introduced to the treatment region TR. The sharpened distal tip of the ablation probe 112 or sharpened distal tip of the trocar facilitates introduction to the treatment region TR in this case. Because the stylet 110, ablation probe 112 or trocar are sufficiently rigid, i.e., have a sufficient column strength, the cannula 108 need not be rigid, but instead can be flexible if desired.

Figure 12B:
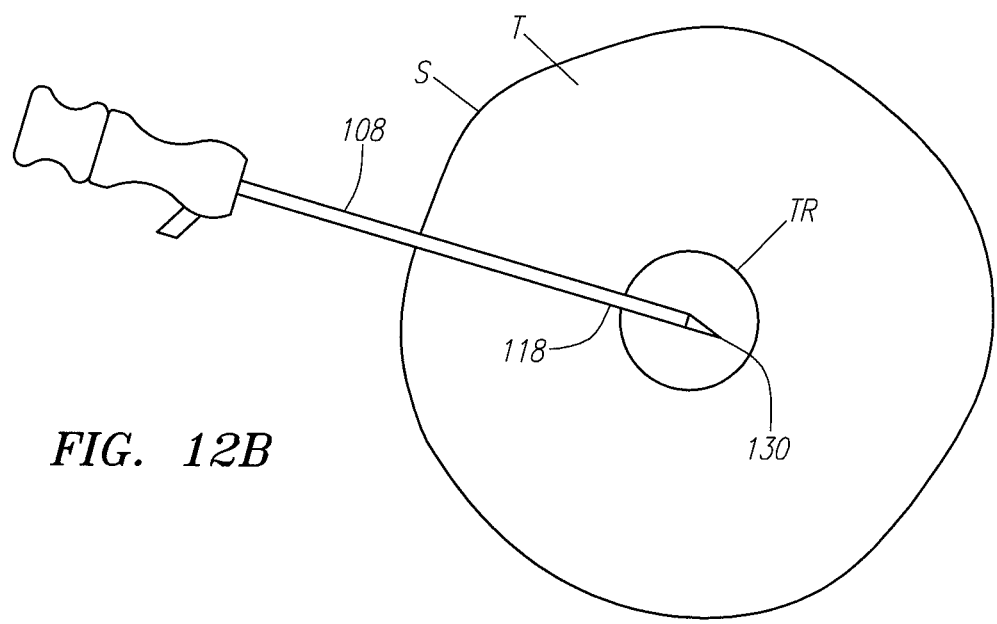

If the ablation probe 112 or trocar, instead of the stylet 110, is used to introduce the delivery cannula 108 to the treatment region TR, the stylet 110 can be exchanged for the ablation probe 112 or trocar. In particular, the ablation probe 112 or trocar are removed from the delivery lumen 120 of the cannula 108, and then the stylet 110 is introduced into the delivery lumen 120 of the delivery cannula 108. After the delivery cannula 108 is properly placed with the distal tip 130 of the biopsy stylet 110 deployed, a sample of the treatment region TR is obtained by distally advancing the delivery cannula 108 over the stylet 110 in order to shear off tissue within the notch 134, as illustrated in FIGS. 12A and 12B. The stylet 110 is then removed from the delivery lumen 120 in order to retrieve the tissue sample for analysis in a laboratory.

Figure 12C:
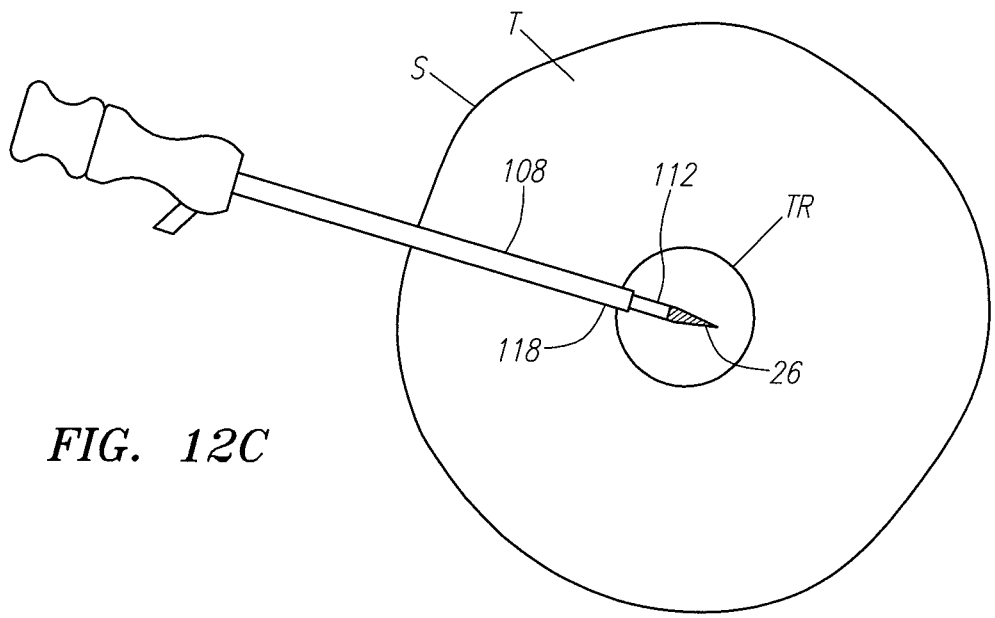
Figure 12D:
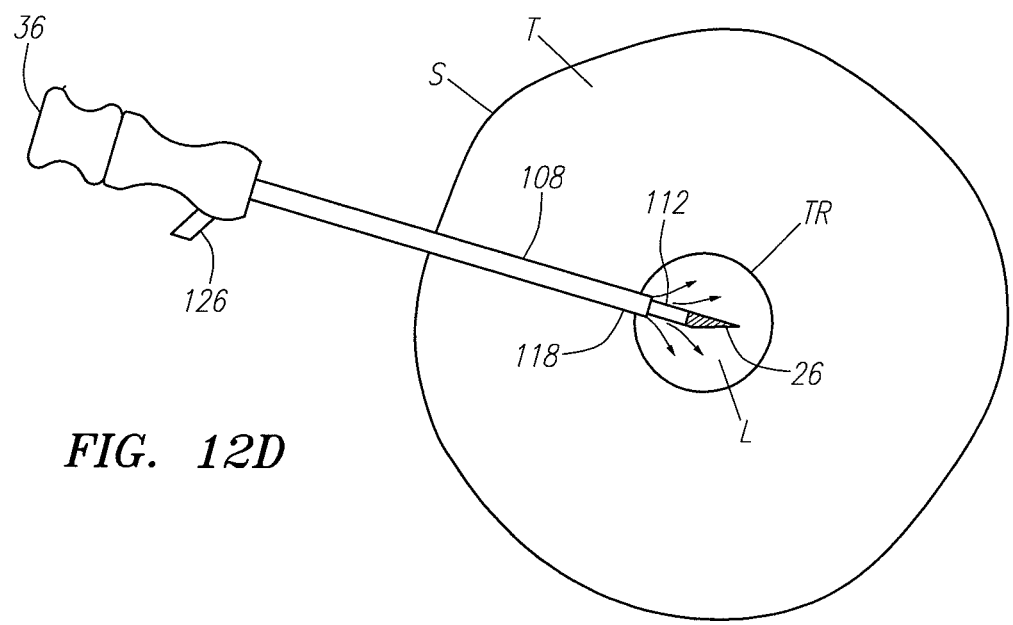
Figure 12E:
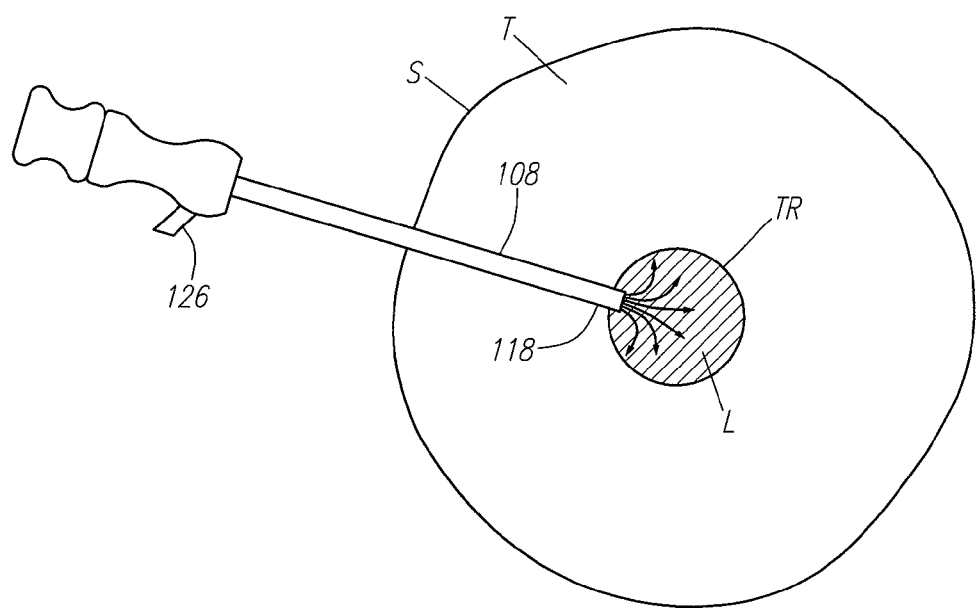

The ablation probe 112 is then introduced through the cannula lumen 120 in a mating arrangement with the delivery cannula 108, so that the electrode 26 extends distally from the cannula 108 into the treatment region TR, as illustrated in FIG. 12C. The RF generator 104 is then connected to the electrical connector 36 on the ablation probe 112, and the pump assembly 16 is connected to the fluid inlet port 126 on the cannula 108, and then operated to ablate the treatment region TR, while perfusing (shown by arrows) the treatment region TR with fluid (FIG. 12D). As a result of the ablation process, a lesion L will be created, which will eventually expand to include the entire tissue region TR (FIG. 12E). Next, one or more chemotherapeutic agents can then be optionally introduced into the fluid inlet port 126 on the cannula 108 to perfuse (shown by arrows) the ablated tissue region TR. Notably, the chemotherapeutic agents can be delivered through the lumens 136 formed between the ablation probe 112 and the cannula 108 or through the delivery lumen 120 of the cannula 108 if the ablation probe 112 has been removed from the cannula 108.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A tissue ablation probe, comprising:
   an elongated cannula having a lumen extending proximally from a distal tip;
   an electrically conductive probe shaft slidably disposed within the lumen of the elongated cannula, an array of electrode tines carried by a distal end of the inner probe shaft; and
   an electrically insulative outer sheath disposed on an exterior surface of the probe shaft, wherein the sheath has thickened regions forming alternating shearable ribs and depressions that longitudinally extend along the probe shaft, the shearable ribs configured to shear off as the probe shaft is introduced through a delivery device, wherein a sheared off rib leaves no portion of the underlying probe shaft exposed.

2. The tissue ablation probe of claim 1, wherein the electrically insulative outer sheath comprises fluorinated ethylene propylene.

3. The tissue ablation probe of claim 1, wherein the electrically insulative outer sheath comprises a heat shrink polymer.

4. The tissue ablation probe of claim 1, wherein the electrically insulative outer sheath comprises a polymer extruded on the probe shaft.

5. The tissue ablation probe of claim 1, wherein the ribs and depressions extend substantially the entire length of the probe shaft.

6. The tissue ablation probe of claim 1, wherein the sheath is fixably disposed on the probe shaft.

7. The tissue ablation probe of claim 1, wherein the probe shaft is cylindrical.

8. The tissue ablation probe of claim 1, wherein the depressions are concave.

9. The tissue ablation probe of claim 1, further comprising an electrical connector carried by a proximal end of the probe shaft, wherein the electrical connector is electrically coupled to the array of electrode tines through the probe shaft.

10. The tissue ablation probe of claim 1, wherein the probe shaft is a cannula, and further comprising an inner probe shaft slidably disposed within the cannula, wherein the array of electrode tines are disposed on the inner probe shaft and deployable from the cannula.

11. The tissue ablation probe of claim 1, wherein the probe shaft is rigid.

12. The tissue ablation probe of claim 1, wherein the probe shaft is removably disposed within the lumen of the cannula, wherein the probe shaft has an outer periphery having a size substantially the same as a diameter of the cannula lumen.

13. The tissue ablation probe of claim 1, wherein the depressions and an inner surface of the cannula cooperate to form a plurality of lumens that longitudinally extend within the cannula.

* * * * *